(12) United States Patent
Darvish et al.

(10) Patent No.: US 6,254,610 B1
(45) Date of Patent: Jul. 3, 2001

(54) DEVICE AND METHOD FOR DRAGGING AND POSITIONING A MEMBER WITHIN A DUCT IN A BODY

(75) Inventors: Nissim Darvish, Haifa; Dov Malonek, Qiryat Tivon, both of (IL)

(73) Assignee: Impulse Dynamics N.V., Curacao (AN)

( * ) Notice: Subject to any disclaimer, the term of this patent is extended or adjusted under 35 U.S.C. 154(b) by 0 days.

(21) Appl. No.: 09/317,589

(22) Filed: May 24, 1999

(51) Int. Cl.$^7$ .................................................. A61F 11/00
(52) U.S. Cl. .................................. 606/108; 606/1
(58) Field of Search ...................... 606/1, 108, 129, 606/200, 127

(56) References Cited

U.S. PATENT DOCUMENTS

| | | | |
|---|---|---|---|
| 5,667,514 | * 9/1997 | Heller | 606/108 |
| 5,868,754 | * 2/1999 | Levine et al. | 606/108 |
| 5,947,995 | * 9/1999 | Samuels | 606/200 |
| 6,001,118 | * 12/1999 | Daniel et al. | 606/200 |

* cited by examiner

Primary Examiner—Linda C. M. Dvorak
Assistant Examiner—Jocelyn Debra Ram
(74) Attorney, Agent, or Firm—Cowen, Liebowitz & Latman, P.C.; William H. Dippert

(57) ABSTRACT

A device for dragging and positioning of a member within a duct in a body comprising a rod, having a proximal end and a distal end, wherein the distal end of the rod is coupled to a loop, designed to be slidably mounted over a guidewire, and wherein said loop is provided with hooking means, onto which a member to be guide and positioned within a duct in a body is hooked, so that when advancing the rod from its distal end, the loop slides forward over the guidewire, and drags the member to the desired target location.

7 Claims, 14 Drawing Sheets

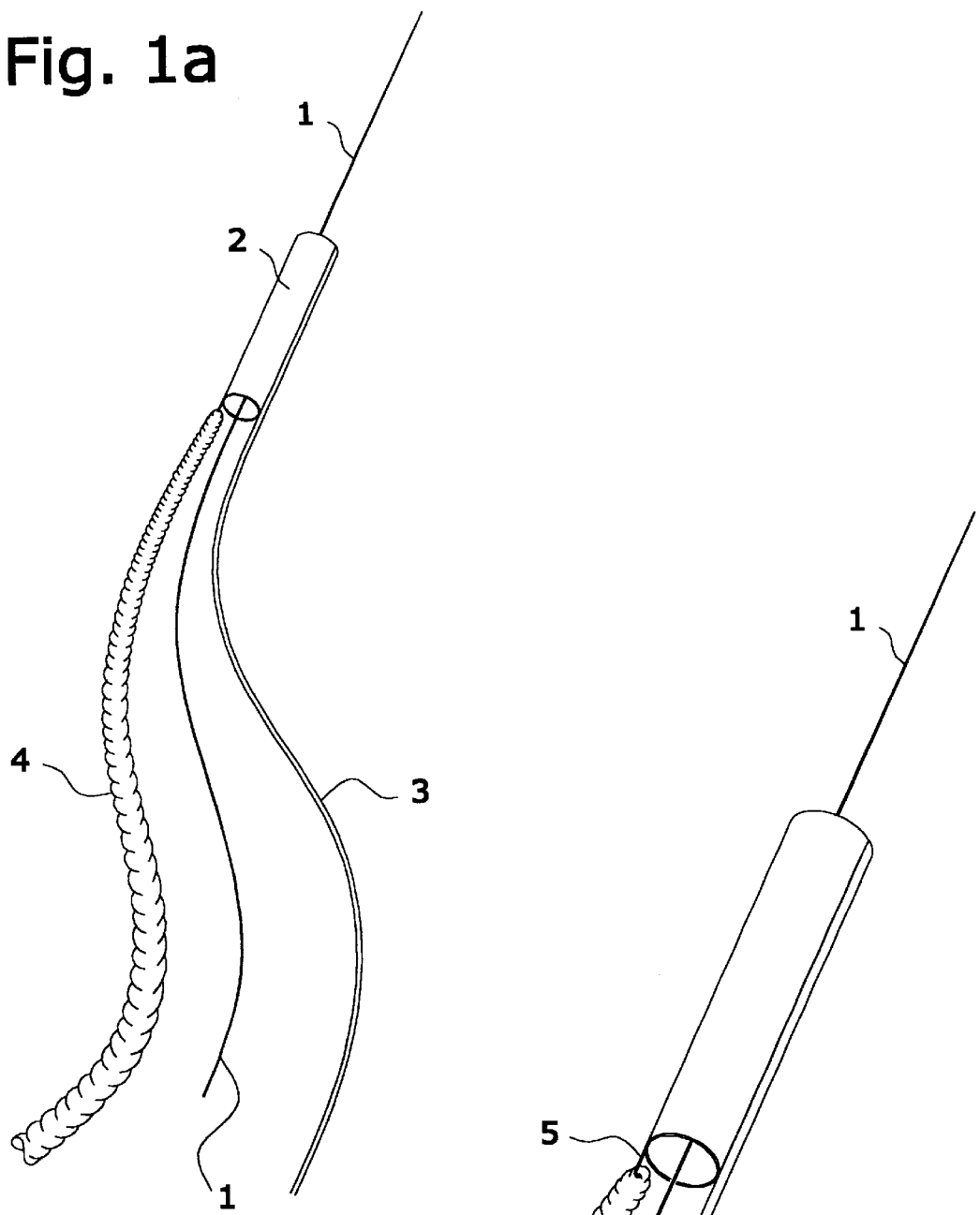
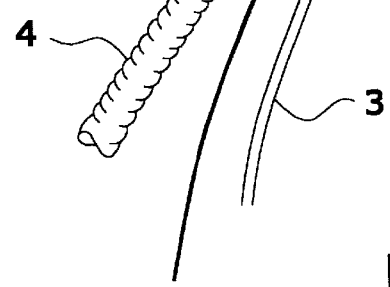

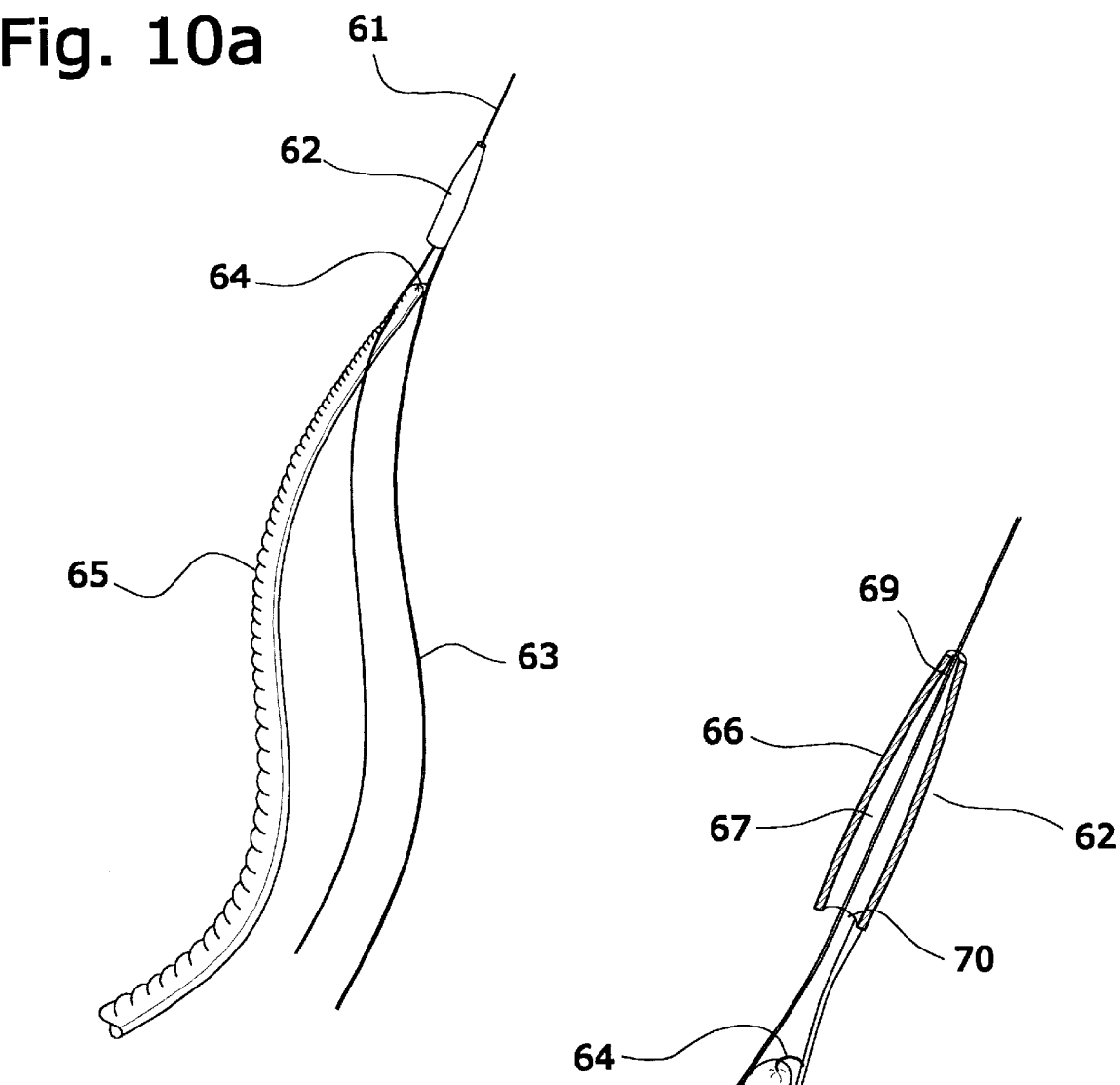

Fig. 11a
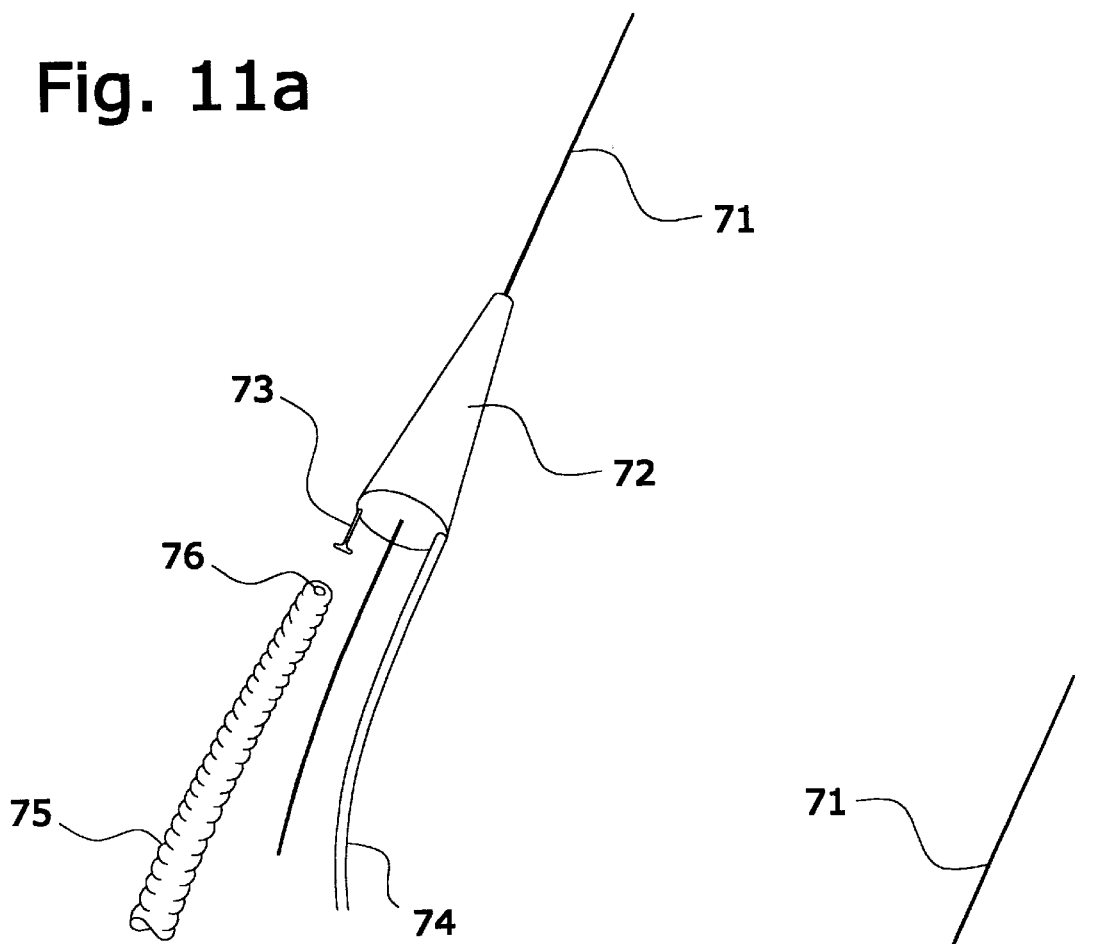
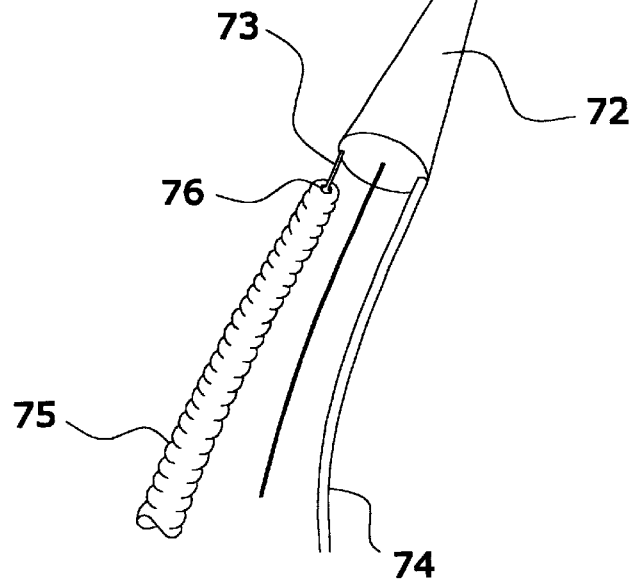
Fig. 11b

Fig. 14a
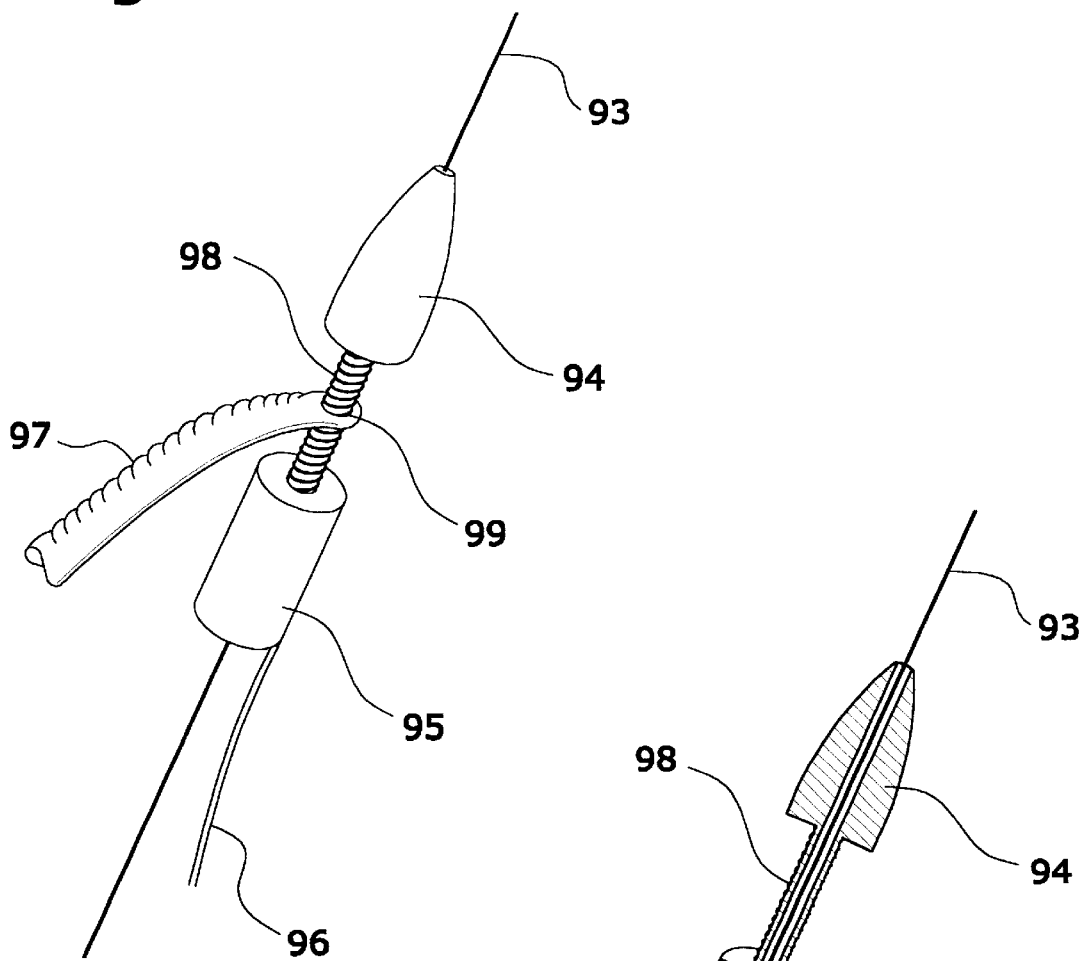
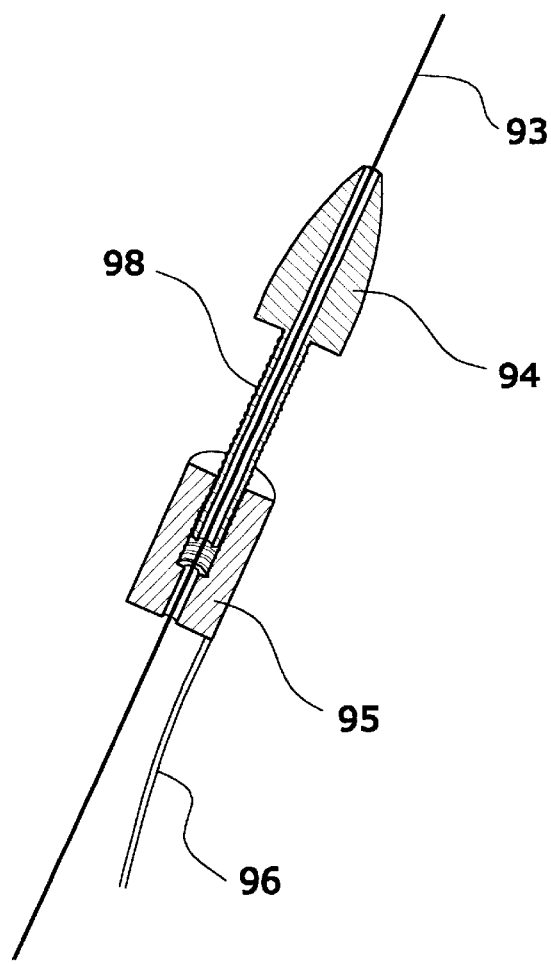
Fig. 14b

DEVICE AND METHOD FOR DRAGGING AND POSITIONING A MEMBER WITHIN A DUCT IN A BODY

FIELD OF THE INVENTION

The present invention relates to the introduction of devices into a duct in a body. More particularly it relates to a dragging and positioning of a member within a duct in a body by employing a pulling mechanism.

BACKGROUND OF THE INVENTION

In general, each device that is introduced into the different body cavities has specific physical properties that are associated with the requirements for its intended use (e.g. angiography catheters, angioplasty balloon, ultrasonic transducer). In addition to the constrains imposed by the intended use, the geometry of such devices is dictated by the physical characteristics of the target position (e.g. blood vessels, atrium, ventricle, bladder, uterus etc.). Similarly, the means of introduction into the target position dictated the mechanical properties of the device and particularly its shaft (e.g. stiffness of the shaft, flexibility of the tip).

For example, pacing electrodes are introduced into the right ventricle or atrium to deliver electrical energy into the cardiac muscle. The conductors that connect the electrodes to an external or implantable pacemaker need to pass through the venous system to endure remarkable mechanical stress, causing probable fatigue due to the cardiac contractions. In order to impart the electrode lead durability the leads are constructed in coil structures that are very flexible and have very high fatigue resistance. The flexibility of the pacemaker lead makes it a difficult task to introduce it into the heart. A popular method of insertion employs a stiffening stylet, which is inserted into the lead during the deployment of the lead and thus increasing the stiffness during the insertion process. Once the lead has been positioned, the stylet is withdrawn and the lead regains its soft nature.

A different device that is introduced into the heart is the angioplasty balloon. The balloon is introduced into the coronaries, inflated at the desired location and then removed. The functional requirement for the balloon is to be capable of inflation and deflation at high reliability. To do so, a tube is connected between the pump and the balloon used for transferring the pressurized air to the balloon. In addition, the balloon needs to be inserted to its target location and thus the tube has a stiff structure to allow its navigation in the blood vessels from the proximal end located externally to the body.

In both examples the stiff body is required only for the insertion process and is not required for the proper operation of the devices once in place.

When administering interventional medical treatment within the human vasculature, or other body ducts, it is sometimes needed to perform a fast exchange of catheters during the operation. In practicing angioplasty, for example, it is often required to exchange one dilatation catheter with another. The exchange must, of course, be carried out fast, to avoid long exposure of the patient's open vasculature to possible infection, and shorten surgery time.

In the known "over-the-wire" catheterization procedure it is necessary to use a long guidewire, typically of 300 cm, which requires two operators to perform the procedure. This procedure is lengthy and prone to mistakes by the operators, as the device may accidentally touch the floor and may be subjected to contamination, which may even require repeating the catheterization procedure again.

In U.S. Pat. No. 5,357,978 (Turk), filed Jan. 12, 1993, an over-the-wire PTCA (Percutaneous Transluminal Coronary Angioplasty) balloon catheter was disclosed, having a guiding wire external to the shaft for slidably mounting over the guidewire. The guiding means has at least two loops, and a guidewire loading attachment between the pair of loops, which snaps onto the shaft of the balloon catheter.

In U.S. Pat. No. 5,040,548 (Yock), filed May 24, 1991, it was disclosed an angioplasty method consisting of the following steps: inserting a guiding catheter within the patient's cardiovascular system, disposing a guidewire within the inner lumen of said guiding catheter, disposing within the inner lumen of the guiding catheter a dilatation catheter having beside its lumen for directing the inflation liquid to the balloon a second shorter lumen, extending through the interior of the balloon, in which the guidewire is slidably disposed; advancing the dilatation catheter within the patient's coronary artery over the guidewire; withdrawing the dilatation catheter over the guidewire and removing it from the guidewire. In this patent, instead of using the "over the wire" approach which requires long exchange wires, the invention utilize a "monorail" approach that allows performing the procedure with shorter exchange wires. This is due to the basic difference between an "over the wire" approach and the "monorail" approach. The engagement between the angioplastic device and the exchange wire in a typical "over-the-wire" device is present throughout the entire length of the angioplastic device while in a typical "monorail" device the attachment between the angioplasty device and the guidewire is achieved over a short segment at the distal tip of the angioplastic device.

In U.S. Pat. No. 5,389,087 (Miraki) filed Jun. 29, 1992, it was disclosed a fully exchangeable over-the-wire catheter with rip seam and gated side port. The catheter is provided with a lumen adapted to receive a guidewire throughout the longitudinal extent of the tubular shaft. The tubular shaft may be provided with a longitudinal rip seam extending into the lumen, which enables the catheter to be peeled from the guidewire during removal and exchange procedures. Optionally the catheter is also provided with one or more side ports into the guidewire lumen.

In U.S. Pat. No. 5,578,009 (Kraus et al.), filed Jul. 20, 1994, it was disclosed an elongated rod, terminating in an abutment device with a lumen for passing of a guidewire, used to push an angioplasty balloon along the guidewire. U.S. Pat. No. 5,718,680 (Kraus et al.), filed as continuation-in-part to U.S. Pat. No. 5,578,009 on Aug. 21, 1996, disclosed a method for placing an angioplasty balloon in accordance with the device disclosed in U.S. Pat. No. 5,578,009.

The advantage of the "monorail" approach comes at the cost of increased risk for damaging the guiding wire during the pushing operation. The proximal end of the advancing angioplastic device may be at some distance from the guide wire and cause it to bend, creating a "kink" that may render the guidewire not fit for further use, and prevent completing the positioning of the angioplasty device in its target location. The invention descried in U.S. Pat. No. 5,040,548 utilizes a large diameter-guiding catheter through which the short guide wire and the angioplastic device are inserted. This catheter minimizes the operational diameter, reducing the distance between the body of the angioplastic device and the guidewire and thus minimizes the above-mentioned potential complication. Thus the employment of a monorail device seems to solve the problem of long exchange wires at the cost of increased diameter of the guiding catheter. There is therefore a need for an apparatus that overcomes both difficulties.

BRIEF DESCRIPTION OF THE INVENTION

In general, it is the object of the present invention to provide a device and a method for guiding and positioning a member within a duct in a body.

It is another object of the present invention to provide device and a method for guiding and positioning a member within a duct in a body that facilitates fast exchange of said member.

Another object of the present invention is to provide a device and method for positioning flexible soft elongated devices.

Another object of the present invention is to provide a device and method for positioning and fast exchanging of flexible devices which possess no or little axial rigidity, and thus cannot be pushed forward by applying force at the proximal end of the device.

Another object of the invention is to provide a device and method that will allow for minimal opening in the blood vessel during procedure.

Therefore, in accordance with a preferred embodiment of the present invention, a device for dragging and positioning of a member within a duct in a body comprising a rod is provided, having a proximal end and a distal end, wherein the distal end of the rod is coupled to a loop, designed to be slidably mounted over a guidewire, and wherein said loop is provided with hooking means, onto which a member to be guides and positioned within a duct in a body is hooked, so that when advancing the rod from its distal end, the loop slides forward over the guidewire, and drags the member to the desired target location.

Furthermore said said loop comprises a tube.

Furthermore said device is used to guide and position a member, said member being a catheter.

Furthermore said device is used to guide and position a member, said member being an electrode lead.

Furthermore said device is used to guide and position a member, said member being an angioplasty balloon.

Furthermore said device is used to guide and position a member, said member being an angioplasty catheter.

Furthermore said hooking means is located at the distal end of the tube.

Furthermore said hooking means are provided with unhooking ability, allowing remote releasing said member by the operator of the device.

Furthermore said rod is provided with a flexible distal end, and has a relatively stiffer main body, to allow it to be advanced by pushing its distal end forward.

Further said rod is provided with a spring at its distal end.

Further said rod is telescopically assembled.

Further said loop comprises a truncated cone.

Furthermore said truncated cone's narrower end fits the width of said guidewire, allowing some additional internal room for the guidewire, so as to enable smooth traveling over the guidewire.

Furthermore said truncated cone is provided with a resilient tube at its distal end.

Furthermore said resilient tube is a coiled spring.

Furthermore a device for dragging and positioning of a member within a duct in a body is disclosed comprising a rod, having a proximal end and a distal end, wherein the distal end of the rod is coupled to a loop, designed to be slidably mounted over a guidewire, and wherein said rod is provided with hooking means, onto which a member to be guided and positioned within a duct in a body is hooked, so that when advancing the rod from its distal end, the loop slides forward over the guidewire, and the member is dragged to the desired target location.

Furthermore said loop comprises a coiled spring.

Furthermore said loop is a tube, made of flexible material.

Furthermore said tube is made of flexible fabric.

Furthermore said loop comprises a first tube having an intrinsic lumen of a predetermined diameter, at whose distal end a second tube whose external diameter fits into said first tube intrinsic lumen is attached.

Furthermore said loop comprises a tube having a gradually narrowing intrinsic lumen.

Furthermore said hooking means comprise a T-shaped flexible member wherein the lateral tips of said T-shaped flexible member can be brought closer by exerting external force, and inserted into a perforation in the member to be guided and positioned within the duct.

Furthermore said hooking means comprise a second loop, provided on said rod, aligned with said first loop so as to allow the passing of said guidewire through both loops, wherein a gap is provided between said loops so that the distal end of said member, may be positioned in said gap, and said guidewire threaded through a perforation at said distal end of said member, to allow dragging of said member by said device when the rod is advanced forward.

Furthermore said hooking means comprise a second loop mounted over said guidewire, said second loop provided with a spike that can be firmly attached to said first loop, by means of insertion into a bore in said first loop, and wherein said member is impaled at its distal end on the spike, prior to its insertion into said bore.

Furthermore said hooking device comprises a cap provided with a tubular extension, said tubular extension provided with external threading, and a lumen that passes through the cap and the extension, and wherein said loop is provided with a barrel with matching internal threading into which said extension may be screwed into.

Furthermore a method for dragging and positioning of a member within a duct in a body is disclosed, consisting of the following steps:

Inserting and positioning a guidewire within the duct, so that its distal end is positioned at the desired target position, and its proximal end is kept outside the duct available for dealing with by the user;

Inserting a dragging device, comprising an elongated rod provided with a loop at its distal end, wherein said loop is slidably mounted over the guidewire;

Attaching the member to be guided and positioned within said duct in a body to said rod distal end; and Advancing said rod into the duct in a body with the member being dragged by it and positioning said member in the target location.

And finally said member is exchanged with another member, by retracting and removing said device and member from said duct, discarding said member, hooking said another member onto said hooking means, and dragging and positioning said another member by said device to the target location.

BRIEF DESCRIPTION OF THE FIGURES

FIG. 1 illustrates a device for dragging and positioning of a member within a duct in a body, in accordance with a preferred embodiment of the present invention. FIG. 1a is a general view of the device. FIG. 1b depicts the distal end of the device, showing its features in detail.

FIG. 10 illustrates a device for dragging and positioning of a member within a duct in a body, in accordance with another preferred embodiment of the present invention, wherein the loop comprises a tube having a tapered intrinsic lumen.

FIG. 11 illustrates a device for dragging and positioning of a member within a duct in a body, in accordance with another preferred embodiment of the present invention, provided with a T-shaped hooking device.

FIG. 14 illustrates a device for dragging and positioning of a member within a duct in a body, in accordance with another preferred embodiment of the present invention, provided with a screw-on-top type of hooking device.

DETAILED DESCRIPTION OF THE INVENTION AND FIGURES

Figure 2:
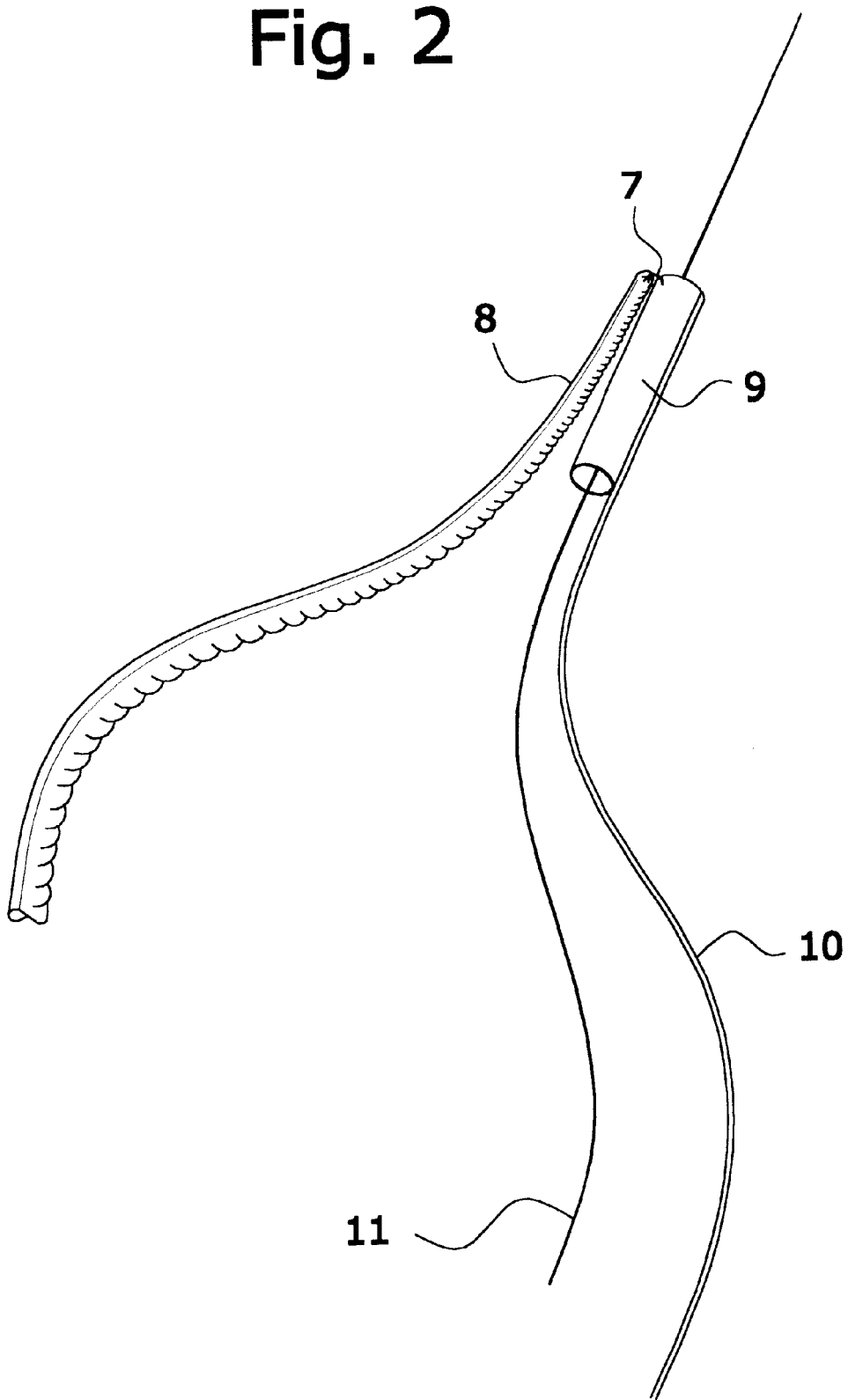
FIG. 2 illustrates another configuration of a device for dragging and positioning of a member within a duct in a body, in accordance with a preferred embodiment of the present invention, with hooking means at the tube's distal end.

The basic provision in the present invention is that instead of pushing forward, or applying force which is transferred forward along an elongated body, while guiding and positioning it within a duct in a body, a pulling mechanism is employed, thus in effect allowing the dragging of the member to be positioned within the duct in a body, and advancing it regardless of its elastic properties. This enables the introduction of soft members within a duct in a body, possessing no or very little axial rigidity or stiffness, and even small members who do not possess an elongated body.

In principle, a device for dragging and positioning of a member within a duct in a body, in accordance with a preferred embodiment of the present invention comprises a stiffened flexible elongated rod, having a proximal end and a distal end, wherein the distal end of the rod is provided with a loop, designed to be slidably mounted over a guidewire, and wherein said loop is provided with hooking means, onto which a member to be guided and positioned within a duct in a body is hooked, so that when advancing the rod from its distal end, the loop slides forward over a guidewire, and drags the member to the desired target location.

Reference is now made to FIG. 1, illustrating a device for dragging and positioning of a member within a duct in a body, in accordance with a preferred embodiment of the present invention. FIG. 1a is a general view of the device.

The device for dragging and positioning of a member within a duct in a body, comprises an elongated, flexible rod (3) possessing axial stiffness to allow its advancement by pushing its proximal end forward, provided with a loop comprising a short tube (2), slidably mounted over a guidewire (1), which is to be guided into said duct and positioned prior to the employment of the device of the present invention. The member to be guided and positioned within the duct—here a catheter (4)—is attached to the tube (2). When the rod (1) is advanced by pushing its proximal portion, the tube (2) is restricted and guided by the guidewire (1) and the catheter (4) is dragged by the tube to its target location. FIG. 1b depicts the distal portion of the device, showing its features in detail. The tube (2) is provided with hooking means (5) onto which the catheter (4) is hooked prior to its insertion within the duct, so as to reliably secure the attachment of the catheter (4) to the tube and prevent disengagement of the catheter from the device while advancing it along the guidewire.

The hooking means may be of a permanent nature, in which case the member is dragged by the device of the present invention, guided into the duct in a body and positioned in the target location. It then performs its task and removed by retracting the device of the present invention, causing the consequent withdrawal of the member too. The member stays hooked to the device throughout the entire operation until its removal from the duct.

The use of the device of the present invention brings about the ability to introduce soft members into a duct in a body. Such soft bodies may be any kind of catheters whose physical properties are optimized for the intended use (e.g. angioplasty balloon, angiography catheter, pacemaker lead, electric control electrode lead, electro-physiological catheter, other electrode leads, etc). The physical property of stiffness needs not be optimized for the torque transmission not for body stiffness but rather for softness. The soft body of the member shall allow for it's a-traumatic residence in the duct in a body and during introduction. Angioplasy balloon inserted by a dragging and positioning device in accordance with the present invention may have a soft tube attached to it for pressure transmission during the inflation of the balloon (such as the one described in U.S. Pat. No.

5,718,680). Angiography catheter inserted by a dragging and positioning device in accordance with the present invention may have a soft tube for radiographic dye insertion. The tube may have a small diameter, as the stiffness of the walls is irrelevant for the insertion of the device and can therefore be overlooked in the design. A pacing lead inserted using a dragging and positioning device in accordance with the present invention does not require the presence of a central lumen within it, as it is dragged behind the distal end of the a dragging and positioning device. At present pacing leads are provided with a lumen for a stiffening stylet insertion during the introduction process. The space that is currently used for stylet insertion can be saved and thus provide thinner leads or else it may be used for additional conductors and electrodes.

Reference is now made to FIG. 2, illustrating another embodiment of a device for dragging and positioning of a member within a duct in a body, in accordance with a preferred embodiment of the present invention, with hooking means of the tube's distal end. The hooking means (7), which hooks to the catheter (8) is positioned at the distal end of the tube (9). This configuration enables the guiding and positioning of the member and withdrawing the guiding device while the member remains in position. In order to achieve that, the hooking means is provided with an unhooking ability, activated by the user from the proximal end of the rod.

Figure 3:
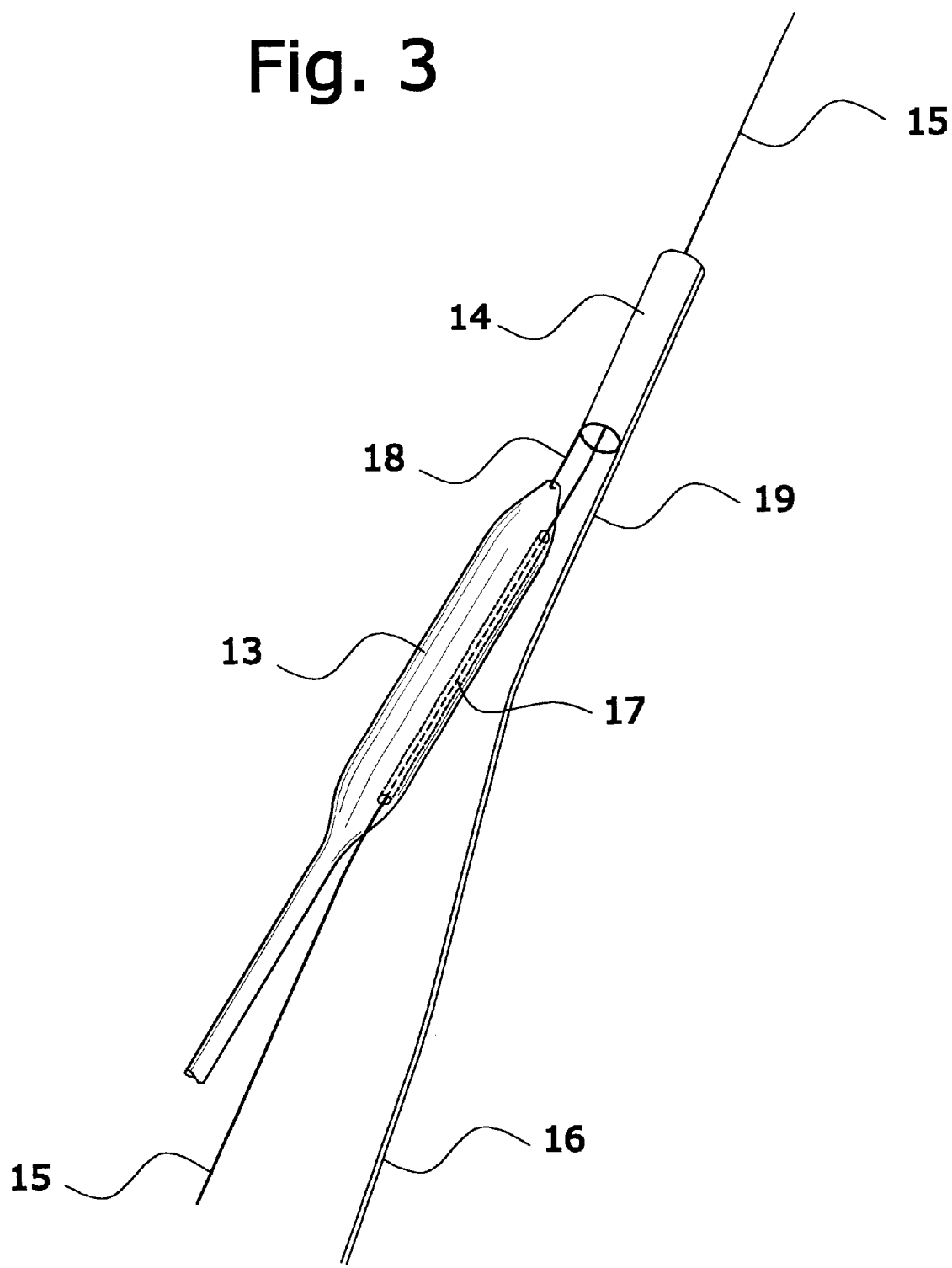
FIG. 3 illustrates a device for dragging and positioning of a member within a duct in a body, in accordance with a preferred embodiment of the present invention used to drag and position an angioplasty balloon, provided with a duct through which the guidewire is passed.

FIG. 3 illustrates a device for dragging and positioning of a member within a duct in a body, in accordance with a preferred embodiment of the present invention, used in dragging and positioning of an angioplasty balloon, provided with a duct through which the guidewire is passed.

The angioplasty balloon (13) is provided with a duct (17), through which the guidewire (15) is passed. The device for dragging and positioning (19) comprises an elongated rod (16), which is provided with a tube (14) at its distal end, which is mounted slidably over the guidewire (15). The tube is provided with a hooking means (18), and the angioplasty balloon (13) is hooked at its distal end to the hooking means (18). As the device is advanced forward, by pushing the rod (16) from its proximal portion, the balloon is dragged behind the tube, and brought to the desired target location.

Figure 4:
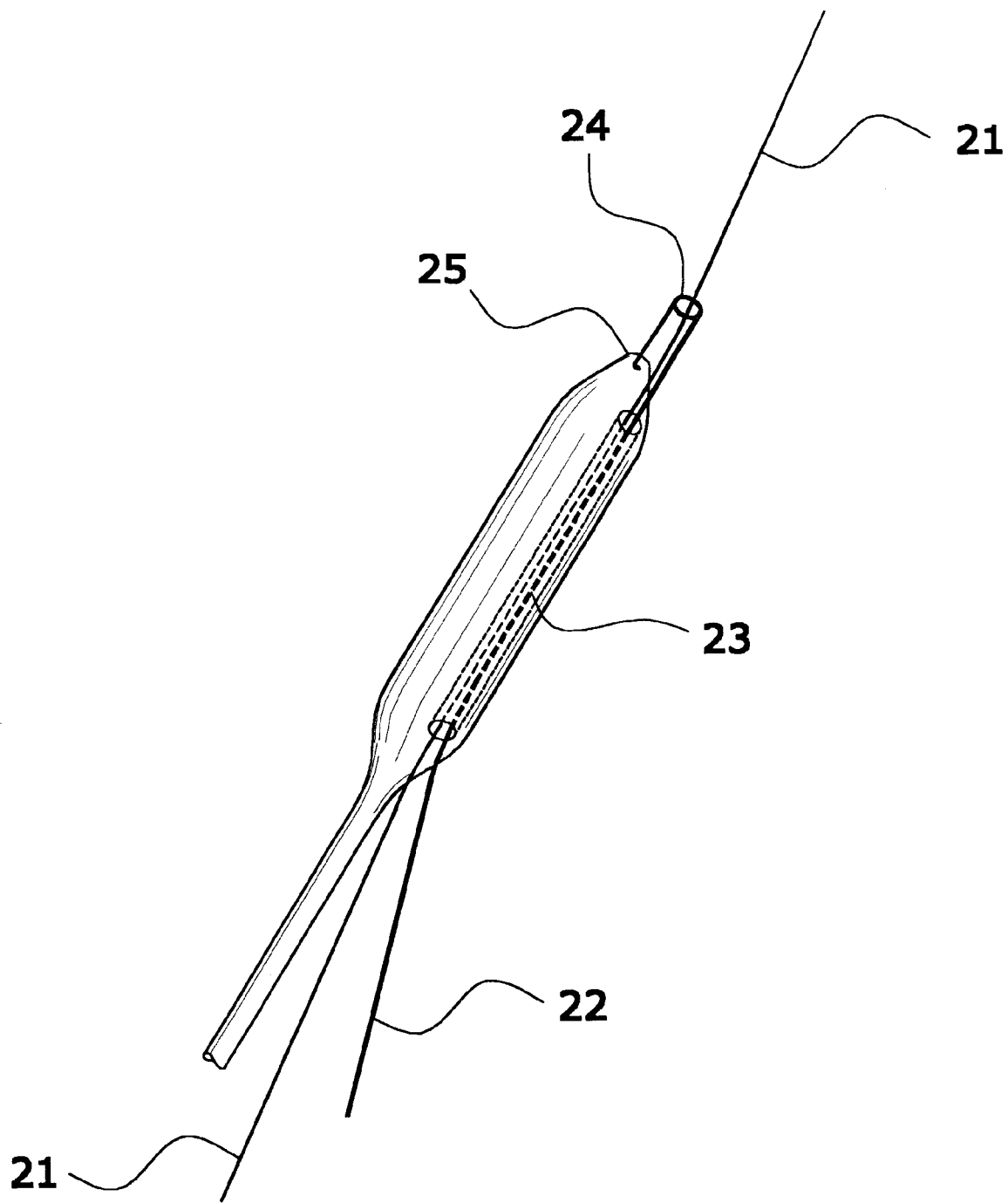
FIG. 4 illustrates a device for dragging and positioning of a member within a duct in a body, in accordance with another preferred embodiment of the present invention, used to drag and position an angioplasty balloon, wherein the rod of the device is passed through a duct within said angioplasty balloon, through which the guidewire also passes.

FIG. 4 illustrates a device for dragging and positioning of a member within a duct in a body, in accordance with a preferred embodiment of the present invention, used to drag and position an angioplasty balloon, wherein the rod of the device is passed through the duct through which the guidewire also passes.

The angioplasty balloon (20) is provided with a duct (23), and the balloon is mounted slidably over the guidewire (21). The distal end of the device for dragging and positioning according to the present invention is threaded through the duct (23), with the loop (24) over the guidewire (21), and the hooking means (25) hooks to the balloon (20) distal end. The duct (23) provides a support for the rod (22) minimizing the risk for the occurrence of a kink along the guidewire, as a result of torque exerted by the device on the guidewire.

In the preliminary process of inserting the guidewire and positioning it in the cardiovascular system, a small diameter guiding catheter, which serves for dye injection for the identification of the coronaries, may be used for guiding the guidewire into the coronaries. After the positioning of the guidewire in its final position, the guiding catheter is removed. Typical ID (Internal Diameter) may be 2F and typical (Outer Diameter) 3F. For most cardiovascular uses the guidewire may be 150 cm long with a diameter of 14 mil.

Figure 5:
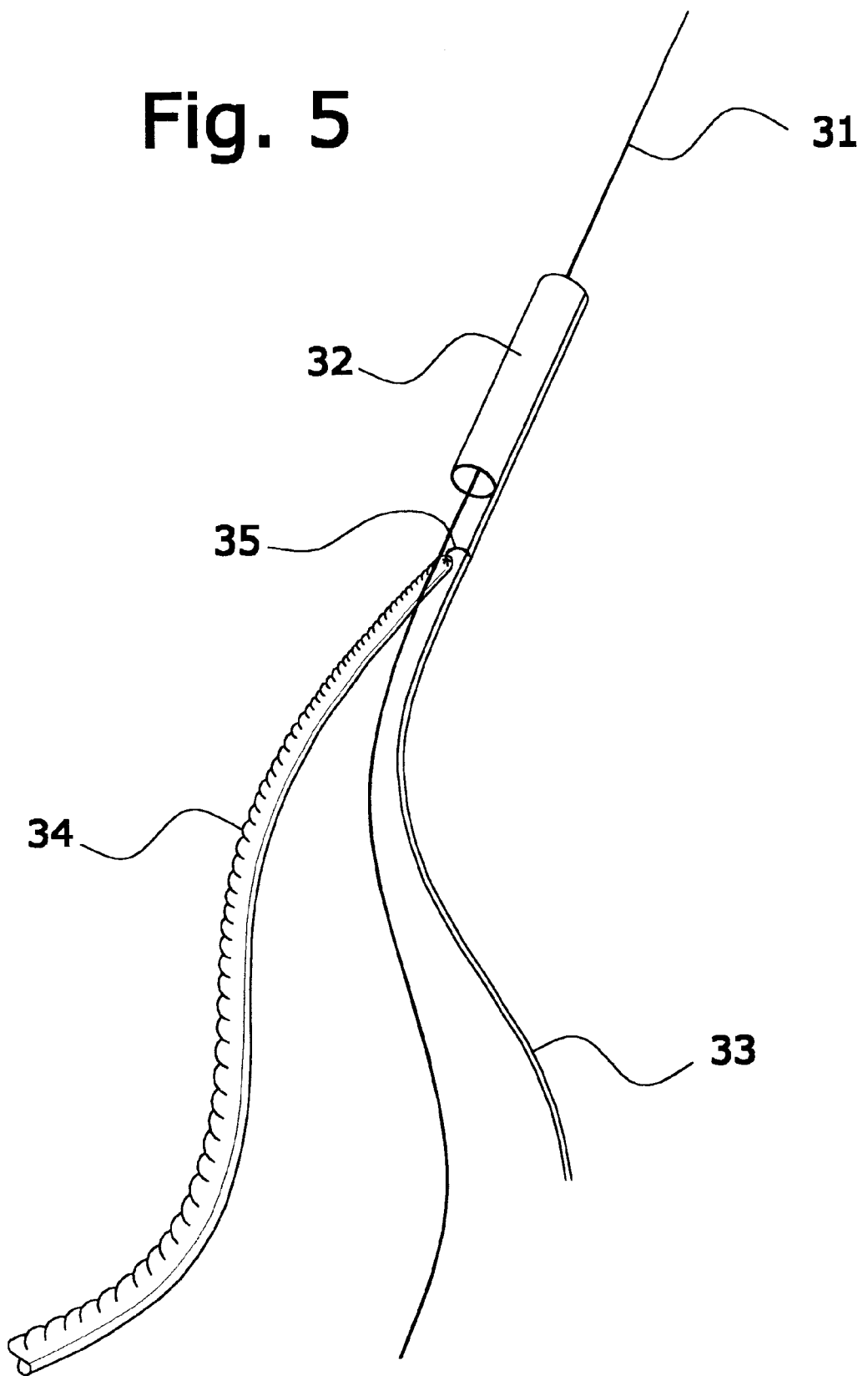
FIG. 5 illustrates a device for dragging and positioning of a member within a duct in a body, in accordance with another preferred embodiment of the present invention, with a hooking means located on the rod.

FIG. 5 illustrates a device for dragging and positioning of a member within a duct in a body. In accordance with another preferred embodiment of the present invention, with a hooking means located on the rod. Here the hooking means (35) is provided on the rod (33) itself, positioned behind the guiding tube (32). This way the tube may be made of soft flexible materials, even such as a flexible fabric, as the risk of tearing the tube (32) resulting from shearing force exerted by the hooking device is eliminated. The tube is not assigned the task of pulling the catheter (34), and it is solely designed to follow the guidewire (31) and slidably move over it.

Figure 6:
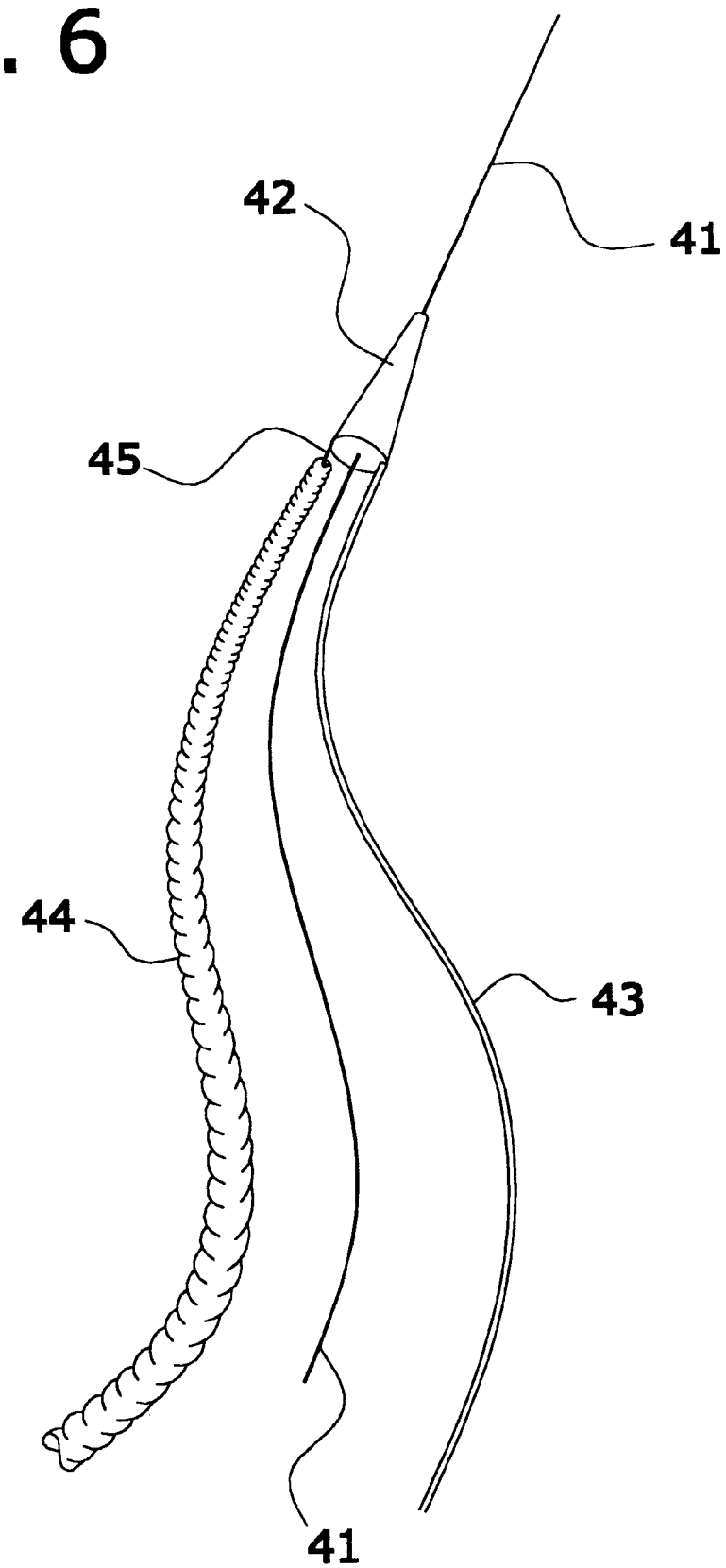
FIG. 6 illustrates a device for dragging and positioning of a member within a duct in a body, in accordance with another preferred embodiment of the present invention, wherein the loop comprises a truncated cone.

FIG. 6 illustrates a device for dragging and positioning of a member within a duct in a body. In accordance with another preferred embodiment of the present invention, wherein the loop comprises a truncated cone. The loop, comprising a truncated cone (42) is attached at the distal end of the rod (43), and is provided at its wider end with hooking means (45), onto which the member to be positioned—here a catheter (44)—is hooked.

It should be noted that the device of the present invention is designed to be inserted into a duct in a body, the body being in particular a human body, and therefore as biological tissue is involved, it is imperative that precautionary measures are taken. The conic shape of the loop minimizes the risk of internal injury inflicted by the loop, as it advances through the duct. The rim at narrower end of the conic-shaped loop (42) is sized to fit the width of the guidewire (41), with only very little additional room, so as to enable smooth traveling over the guidewire. On the other hand, as the internal lumen s becoming wider along the conic-shaped loop towards its proximal end, it exerts substantially less friction on the guidewire and therefore provides a smother introduction of the device into the duct and advancement over the guidewire.

Figure 7:
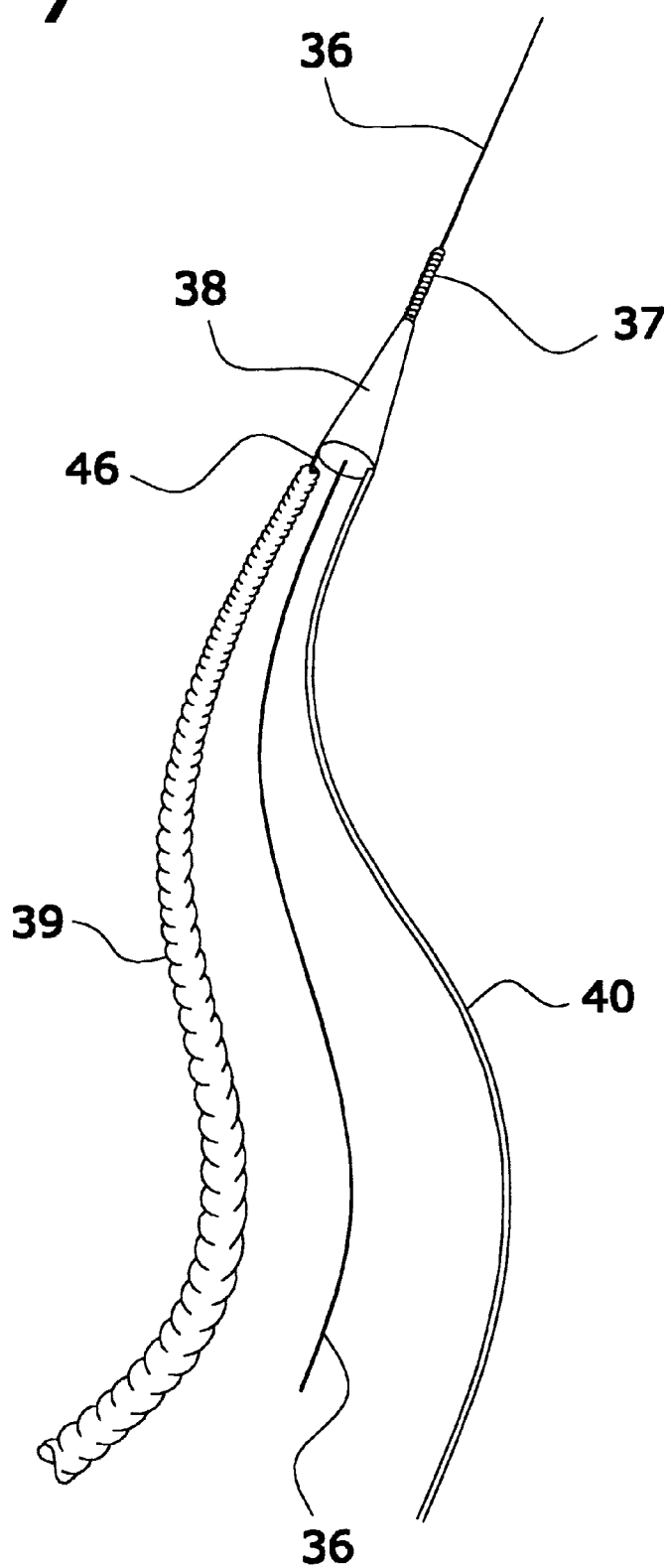
FIG. 7 illustrates a device for dragging and positioning of a member within a duct in a body, in accordance with another preferred embodiment of the present invention, wherein the loop comprises truncated cone, and provided with a resilient tube at its distal end.

FIG. 7 illustrates a device for dragging and positioning of a member within a duct in a body. In accordance with another preferred embodiment of the present invention, wherein the loop comprising a truncated cone, and provided with a resilient tube at its distal end. Here the conic-shaped loop (38 is provided with a coiled spring (37) at its distal tip, which is also slidably mounted over the guidewire (36) when the device is used. The coiled spring enhances the ability of the device to follow turns and twists of the guidewire (36) as it passes through winding passages in the duct. The catheter (39) is hooked onto hooking means (46) positioned at the proximal end of the conic-shaped loop (38), and are dragged behind the loop, and it is advanced by pushing the rod (40).

Figures 8A, 8B:
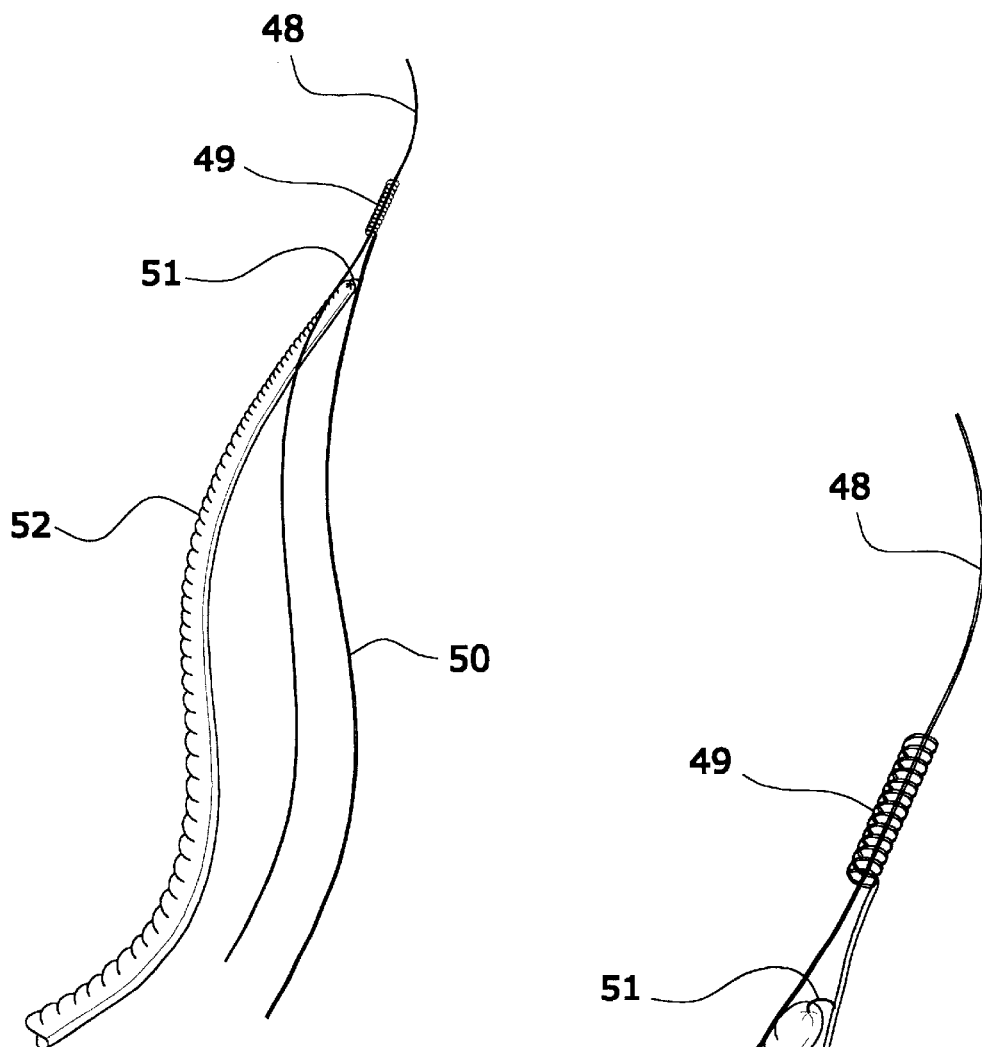
FIG. 8 illustrates a device for dragging and positioning of a member within a duct in a body, in accordance with another preferred embodiment of the present invention, wherein the loop comprises a coiled spring.

FIG. 8 illustrates a device for dragging and positioning of a member within a duct in a body. In accordance with another preferred embodiment of the present invention, wherein the loop comprises a coiled spring. FIG. 8A is a general view of the device, whereas FIG. 8B provides an enlarged view of the device. The advantage in the use of a coiled spring is that it readily adopts the twists and turns that the guidewire presents along the way inside a body duct with substantial curvatures (such as cardiac coronary veins) and submits to the path taken by the guidewire. The coiled spring (49) is attached to a rod (50) at its distal end. On the rod (50) a hooking means (51) is provided, the member to be positioned—here a catheter (52)—is hooked onto. As the rod is pushed forward from its proximal portion (not seen) the coiled spring forces the rod distal end to follow the path of the guidewire, and the catheter (52) drags from behind the coiled spring.

Figure 9A:
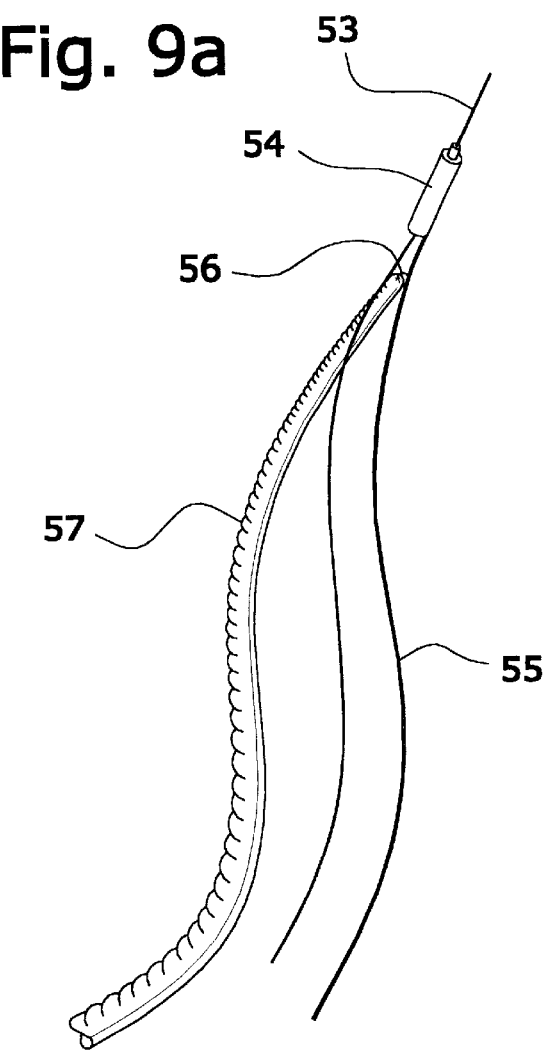
FIG. 9 illustrates a device for dragging and positioning of a member within a duct in a body, in accordance with another preferred embodiment of the present invention, wherein the loop comprises a first tube having an intrinsic lumen of a predetermined diameter, at whose distal end a second tube whose external diameter fits into said first tube intrinsic lumen.
Figure 9B:
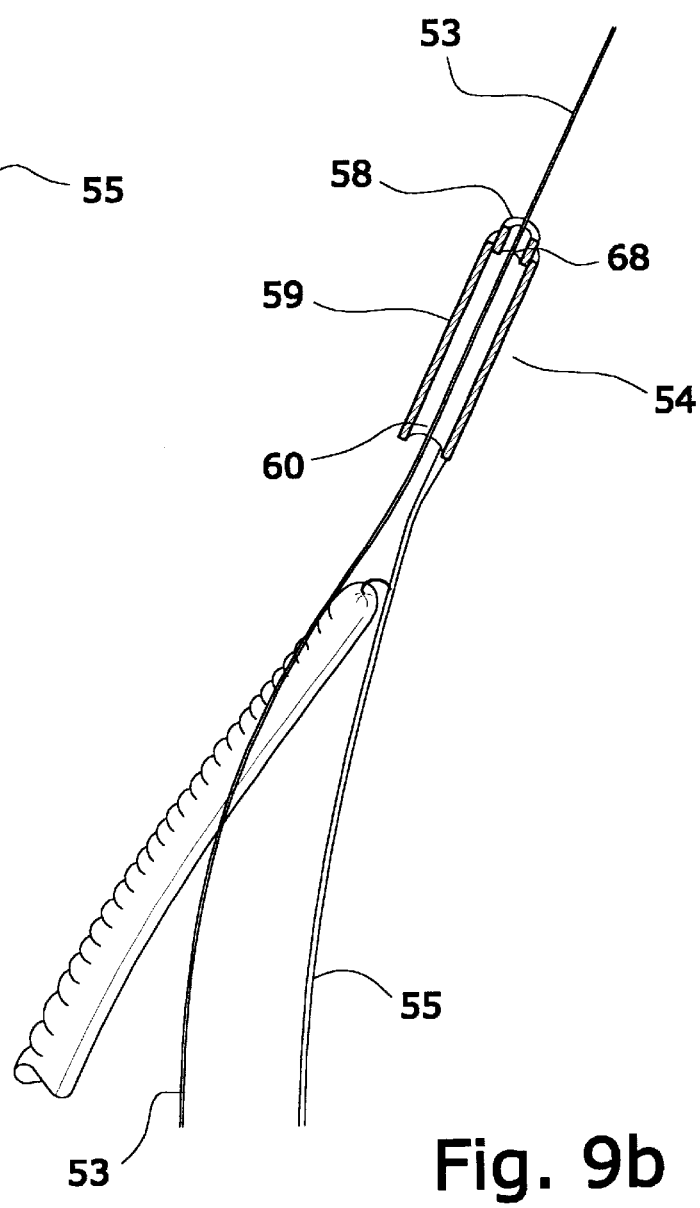

FIG. 9 illustrates a device for dragging and positioning of a member within a duct in a body, in accordance with another preferred embodiment of the present invention, wherein the loop (54) comprise a first tube having an intrinsic lumen of a predetermined diameter, at whose distal end a second tube whose external diameter fits into said first tube intrinsic lumen. FIG. 9A illustrates a general view of the device, and FIG. 9B provides a longitudinal cross-section of the loop. This embodiment seems particularly simple and cheap to manufacture. The loop comprises a first tube (59) having an intrinsic lumen (60) of a predetermined diameter, at whose distal end a second tube (58) with narrower intrinsic lumen (68) whose external diameter fits into said first tube intrinsic lumen. This way the narrower tube holds steadier onto the guidewire (53), allowing it to slide over the guidewire, but preventing wiggling of the distal end of the loop on the guidewire, and thus reducing the risk of jolting and consequently inflicted internal injury. The rest of the loop body, comprising the wider tube, has a little more room around the guidewire, and thus reduces the friction during the advancement of the device over the guidewire. The catheter (57) is hooked onto hooking means (56) located behind the proximal end of the loop, on the rod (55).

a device for dragging and positioning of a member within a duct in a body. In accordance with another preferred embodiment of the present invention, wherein the loop comprises a tube having a gradually narrowing intrinsic lumen. FIG. 10A illustrates a general view of the device, whereas FIG. 10B depicts a longitudinal cross section of the loop of the device. The loop comprises a tube (62) having a gradually narrowing intrinsic lumen (67) defined within the loop wall (66), wherein at its distal end (69) the internal diameter of the lumen is smaller that the internal diameter of the lumen at the proximal end (70). The tube (62) is attached at the distal end of a rod (63), and the rod is provided with a hooking means (64) that the member to be positioned (65) is hooked onto. the tube is slidably mounted over the guidewire (61), so that at the rod (63) is advanced the tube (62) follows the path taken by the guidewire, and the catheter (65) is dragged behind the tube.

The design of the loops described in FIGS. 6, 7, 9, 10 is characterized by the loop comprising an elongated body having an intrinsic lumen, whose distal opening is smaller than its proximal opening. This design is advantageous with respect to friction considerations (as mentioned above) and particularly appealing if the device of the present invention is to be used in blood vessels. In small voids (such as the space left between the internal wall of a tube of constant lumen mounted over a guidewire and that guidewire), blood may clot, and this may endanger the patient (if blood clots start drifting in his bloodstream) and may also impose greater friction between the loop and guidewire, making it more difficult to advance the device along the guidewire (or even withdraw it).

FIG. 11 illustrates a device for dragging and positioning of a member within a duct in a body. In accordance with another preferred embodiment of the present invention, provided with a T-shaped hooking device. The loop, here in the form of a truncated cone (72), is attached to the rod (74), and mounted over guidewire (71). The truncated cone (72) is provided with a hooking means comprising a T-shaped flexible member (73) can be brought closer by exerting external force (e.g. pressing it between two fingers), and inserted into a perforation (76) in the member to be guided and positioned within the duct—here a catheter (75). FIG. 11A illustrates the device prior to engaging the catheter (75) to the hooking means (the T-shaped flexible member (73)), whereas FIG. 11B illustrates the device after hooking the catheter onto the hooking means.

Figure 12:
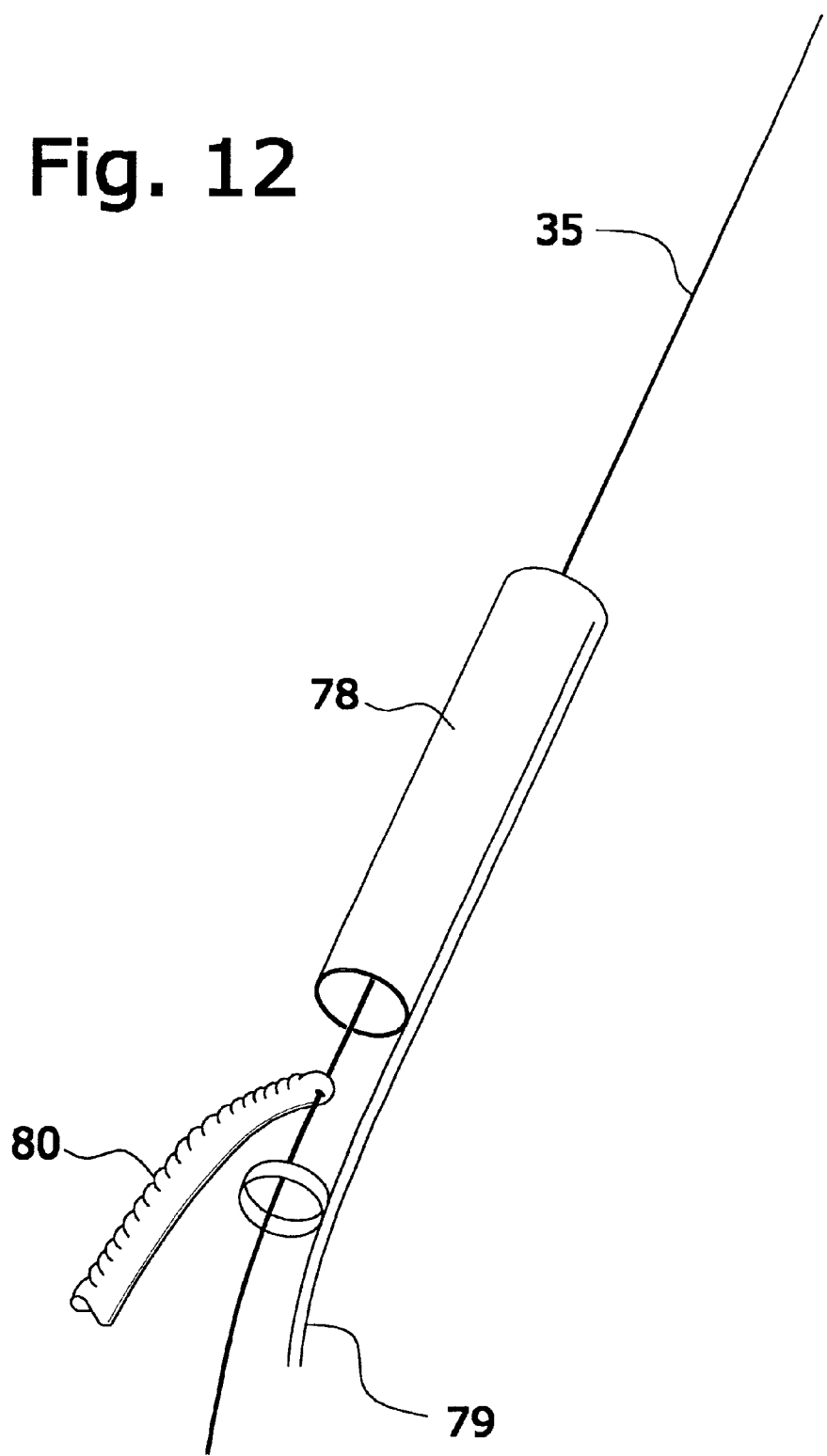
FIG. 12 illustrates a device for dragging and positioning of a member within a duct in a body, in accordance with another preferred embodiment of the present invention, provided with fast release hooking device.

FIG. 12 illustrates a device for dragging and positioning of a member within a duct in a body, in accordance with another preferred embodiment of the present invention, provided with a fast release hooking device. Loop (78), attached to rod (79), is mounted over guidewire (77). The rod is provided with a second loop (82) aligned with the first loop (78), so that guidewire (77) may pass through both loops, and a gap between the two loops is provided so that the distal end (81) of the member to be guided and positioned within the body duct may be—here catheter (80) may be positioned in the gap, and be pierced and the guidewire allowed to pass through the pierced catheter. The engagement of the catheter to the dragging and positioning device is done outside the body duct and once engaged the guidewire is guided to the desired position, and the device is advanced forward along the guidewire to bring the catheter to the desired location. The hooking means described herein is a fast release hooking device, as in order for the catheter to be released from the dragging and positioning device the guidewire is pulled backwards and once the guidewire is withdrawn from the gap between the two loops the catheter disengages from the device, and the guidewire and the dragging and positioning device may be withdrawn and removed.

Figure 13:
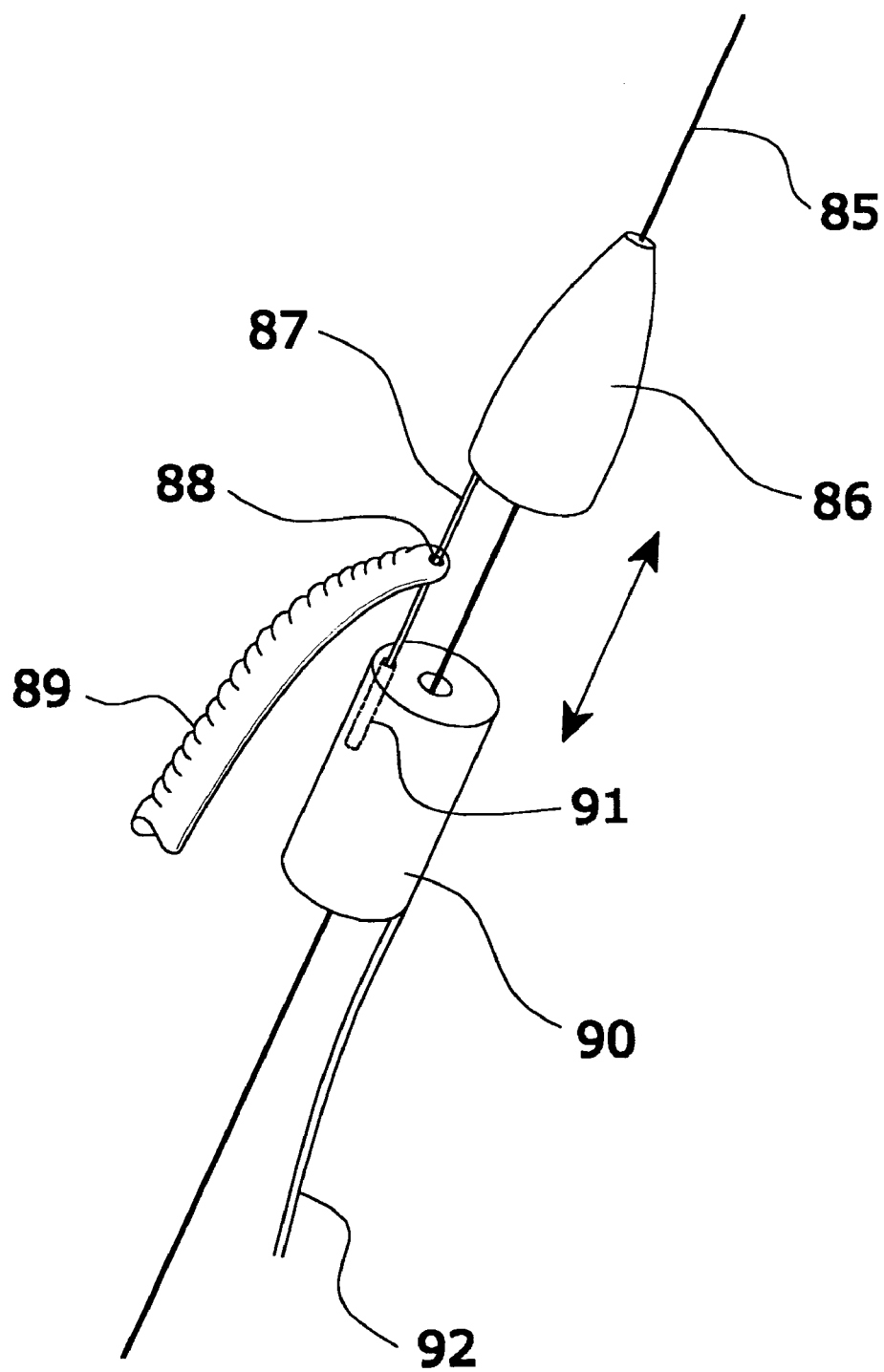
FIG. 13 illustrates a device for dragging and positioning of a member within a duct in a body, in accordance with another preferred embodiment of the present invention, provided with yet another optional hooking device.

FIG. 13 illustrates a device for dragging and positioning of a member within a duct in a body, in accordance with yet another preferred embodiment of the present invention, provided with yet another optional hooking device. Loop (86), mounted over guidewire (85), and provided with a spike (87) that can be firmly inserted into a bore (91) in a second loop, in the form of a tube (90) and held together. The catheter (89) is impaled at its distal end (88) on the spike, prior to its insertion into bore (91). The tube(90), coupled to rod (92), is also mounted over guidewire (85).

FIG. 14 illustrates a device for dragging and positioning of a member within a duct in a body, in accordance with yet another preferred embodiment of the present invention, provided with a screw-on-top type of hooking device. The loop—in the form of a tube (95), coupled to rod (96), is provided with a cap (94), at its distal end. The cap (94) is provided with a tubular extension (98) said tubular extension provided with external threading, and a lumen passes through the cap and the extension. Tube (95) is provided with a barrel with matching internal threading into which extension (98) may be screwed into. The member to be dragged and positioned within the body duct is attached to the extension (98) by threading into which extension through a perforation (99) at the distal end of the catheter (97), and the extension is then screwed in position in tube (95). The guidewire (93) is threaded through the coaxial lumens of the cap (94), the extension (98) and the tube (95), all mounted over the guidewire. FIG. 14A illustrates a general view of the device with a catheter attached, whereas FIG. 14B depicts a longitudinal cross-section view of the device (without the catheter).

FIGS. 11–14 are given for the purpose of illustrating several options for the design of the hooking means for a dragging and positioning device in accordance with a preferred embodiment of the present invention, and it should be noted these may be incorporated with any embodiment of the present invention.

The method of dragging and positioning of a member within a duct in a body, in accordance with the present invention, consists of the following steps:

1. Inserting and positioning a guidewire within the duct, so that its distal end is positioned at the desired target position, and its proximal end is kept outside the duct available for dealing with by the user;
2. Inserting a dragging device, comprising an elongated rod provided with a loop at its distal end, wherein said loop is slidably mounted over the guidewire;
3. Attaching the member to be guided and positioned within said duct in a body to said rod distal end; and
4. Advancing said rod into the duct in a body with the member being dragged by it and positioning said member in the target location.

In case of a fast exchange operation, such as angioplasty operation, it is desired to leave the member (an angioplasty balloon)

The member being dragged into position may be an elongated body, such as a catheter, electrode lead, but it can also be any other object that needs insertion and positioning within a duct in a body, such as an electronic transducer, a micromachine, a chip or any other object that needs insertion and positioning.

A guiding catheter may be used in the case of cardiovascular catheterization, inserted through an introducer into the coronaries. This is a small diameter catheter that will require a small introducer. It has a Luer type fitting on a Y connector for attaching a syringe for radiographic fluid injection for mapping the coronaries. Once the desired branch is identified, the guidewire is pushed forward into its target location, and after completing the positioning of the guidewire, the guiding catheter is withdrawn, leaving the guidewire in place. A small segment of the guide wire is left extending from the introducer and its hemostatic valve.

After the guiding sheath has been removed, the distal loop at the distal end of the dragging and positioning device of the present invention is mounted on the proximal end of the guidewire, and the member to be introduced within the coronaries is hooked onto the hooking means at the loop at the distal end of the device. The guidewire is long enough to grab onto after this stage. The operator grabs onto the proximal side of the guide wire with one hand and pushes forward the rod of the dragging and positioning device with the other hand. Radiographic solution may be injected through the second lumen of the angiographic balloon if mapping of the coronaries is desired. The device is pushed forward, dragging behind it the member to be positioned until it reaches its desired target position.

If an exchange of the member is required, the dragging and positioning device, as well as the positioned member are withdrawn and removed from the duct, while the guidewire remains in position. The old member is discarded, and a second member is hooked onto the hooking means at the distal end of the device, and dragged and positioned in the same manner, repeating the steps of the method as described herein, using the positioned guidewire for navigation towards the target location.

Different embodiments of the dragging and positioning device of the present invention may be constructed. Optionally it may be provided with a flexible distal end that is mounted over the guidewire, in order to prevent injury or damage to the duct, and a relatively stiff proximal end for the pushing operation. Another possibility is to use for the rod of the device a stiff guidewire that has a spring attached to its distal end. Yet another option for the rod of the device is to be of a telescopic type construction that allows for initial short pushing device (and thus short guide wire) that is extended only in the blood vessel.

The loop may be in the form of a simple metallic loop whose inner diameter is sufficient for mounting on the guide wire. Alternatively, the loop may be in the form of a hollow tube. The inner diameter of the tube needs to be large enough to fit onto the guide wire.

The intended purpose of the loop is to slide over the guidewire and drag the member to be positioned behind him. In order to slide over the guidewire, the loop needs to exert minimal friction on the guidewire and on the walls of the internal ducts through which it travels. In addition, it needs to be firmly attached to the member and withstand the pulling forces exerted by the device on the hooking device. These pulling forces result from the friction between the device and the duct through which it is inserted.

It should be clear that the description of the embodiments and attached Figures set forth in this specification serves only for a better understanding of the invention, without limiting its scope as covered by the following Claims.

It should also be clear that a person in the art, after reading the present specification could make adjustments or amendments to the attached Figures and above described embodiments that would still be covered by the following Claims.

What is claimed is:

1. An apparatus for dragging and positioning a medical device within a duct in a body, which is navigated to a target location, using a guide wire previously deployed within the duct, the apparatus comprising:
   a rod having a proximal end and a distal end;
   a looped member coupled to the distal end of the rod, adapted to be slidably mounted over to the guide wire; and
   engaging means for engaging the medical device to the apparatus,
wherein said engaging means comprises a second looped member, provided on said rod, aligned with said first looped member so as to allow the passing of the guide wire through both looped members, wherein a gap is provided between said looped members so that a portion of the medical device, may be positioned in said gap, and said guide wire threaded through a perforation at said portion of said medical device, so as to allow dragging of the medical device by said apparatus when the rod is advanced forward.

2. An apparatus for dragging and positioning a medical device within a duct in a body, which is navigated to a target location, using a guide wire previously deployed within the duct, the apparatus comprising:
   a rod having a proximal end and a distal end;
   a looped member coupled to the distal end of the rod, adapted to be slidably mounted over to the guide wire; and
   engaging means for engaging the medical device to the apparatus,
wherein said engaging means comprises a cap provided with a tubular extension, said tubular extension provided with external threading, and a lumen that passes through the cap and the extension, and wherein said loop is provided with a barrel with matching internal threading into which said extension may be screwed, and wherein when the medical device is engaged to the apparatus and the apparatus is advanced within the duct to the target location, the medical device is dragged by the apparatus and positioned at the target location.

3. A method for dragging and positioning of a medical device within a duct in a body at a predetermined target location, comprising:
   providing a dragging apparatus, comprising an elongated rod provided with a looped member at its distal end, wherein said looped member may be slidably mounted over a guide wire;

deploying a guide wire within the duct, so that its distal end is positioned at the desired target position, and its proximal end is kept outside the duct available for dealing with by the user;

attaching the medical device to be guided and positioned within said duct in a body to said dragging apparatus; and advancing said dragging apparatus into the duct of the body with the medical device being dragged by it until the medical device is positioned at the target location.

4. The method according to claim 3, further comprising exchanging said medical device with a second medical device, by retracting and removing said dragging apparatus and medical device from said duct, discarding said medical device, engaging the second medical device to the dragging apparatus, and dragging and positioning the second medical device by said dragging apparatus to the target location.

5. An apparatus for dragging and positioning a medical device within a duct in a body, which is navigated to a target location, using a guide wire previously deployed within the duct, the apparatus comprising:

a rod, having a proximal end and a distal end;

a looped member in the shape of a truncated cone having a wider end and a narrower end provided with a resilient tube at its narrower end, adapted to slide over the guide wire, the looped member being coupled to the distal end of the rod, adapted to be slidably mounted over the guide wire; and engaging means for engaging the medical device to the apparatus, wherein when the medical device is engaged to the apparatus and the apparatus is advanced within the duct to the target location, the medical device is dragged by the apparatus and positioned at the target location.

6. The apparatus according to claim 5, wherein said resilient tube is a coiled spring.

7. An apparatus for dragging and positioning a medical device within a duct in a body, which is navigated to a target location, using a guide wire previously deployed within the duct, the apparatus comprising:

a rod, having a proximal end and a distal end;

a looped member coupled to the distal end of the rod, adapted to be slidably mounted over to the guide wire; and engaging means, for engaging the medical device to the apparatus, comprising a T-shaped flexible member wherein the lateral tips of said T-shaped flexible member can be brought closer by exerting external force, and inserted into a perforation in the medical device to be guided and positioned within the duct, wherein when the medical device is engaged to the apparatus and the apparatus is advanced within the duct to the target location, the medical device is dragged by the apparatus and positioned at the target location.

* * * * *